United States Patent
Lotan et al.

(10) Patent No.: US 11,963,844 B2
(45) Date of Patent: *Apr. 23, 2024

(54) ORTHODONTIC SYSTEM WITH TOOTH MOVEMENT AND POSITION MEASURING, MONITORING, AND CONTROL

(71) Applicant: Dror Ortho Design LTD, Jerusalem (IL)

(72) Inventors: Tal Lotan, Jerusalem (IL); Shachar Ronen, Jerusalem (IL)

(73) Assignee: Dror Ortho Design Ltd (Aerodentis), Jerusalem (IL)

(*) Notice: Subject to any disclaimer, the term of this patent is extended or adjusted under 35 U.S.C. 154(b) by 356 days.

This patent is subject to a terminal disclaimer.

(21) Appl. No.: 17/087,345

(22) Filed: Nov. 2, 2020

(65) Prior Publication Data
US 2021/0145544 A1  May 20, 2021

Related U.S. Application Data

(62) Division of application No. 15/269,465, filed on Sep. 19, 2016, now Pat. No. 10,820,965.

(51) Int. Cl.
*A61C 7/00* (2006.01)
*A61B 1/00* (2006.01)
(Continued)

(52) U.S. Cl.
CPC ............... *A61C 7/002* (2013.01); *A61B 1/24* (2013.01); *A61B 5/0002* (2013.01);
(Continued)

(58) Field of Classification Search
CPC ......... A61C 7/002; A61C 7/08; A61C 1/0015; A61C 1/0038; A61C 1/0061; A61C 19/05;
(Continued)

(56) References Cited

U.S. PATENT DOCUMENTS

| 3,975,825 A | 8/1976 | Smith |
| 4,823,488 A | 4/1989 | Fottner |

(Continued)

FOREIGN PATENT DOCUMENTS

| EP | 3060159 A1 | 8/2016 |
| JP | 2008-532563 A | 8/2008 |

(Continued)

OTHER PUBLICATIONS

Advisory Action (PTOL-303) received for U.S. Appl. No. 15/269,465, dated Jul. 26, 2018, 03 pages.

(Continued)

*Primary Examiner* — Ralph A Lewis
*Assistant Examiner* — Drew S Folgmann
(74) *Attorney, Agent, or Firm* — Rivka Friedman

(57) ABSTRACT

An orthodontic system and method for aligning at least one tooth of an upper jaw or a lower jaw of a patient. In the system and method at least one orthodontic appliance can be provided which may include at least one force exerting member for applying a force to move the at least one tooth, a tooth movement sensor for obtaining tooth movement data, and a tooth movement monitor for calculating at least one of the distance the at least one tooth has moved and a current position of the at least one tooth from the tooth movement data. An electronic control console may be operatively connected to the force exerting member and in data communication with the tooth movement monitor, for controlling the operation of the force exerting member using the at least one of the distance the at least one tooth has moved and the current position of the at least one tooth.

6 Claims, 7 Drawing Sheets

(51) Int. Cl.
| | |
|---|---|
| *A61B 1/24* | (2006.01) |
| *A61B 5/00* | (2006.01) |
| *A61B 5/11* | (2006.01) |
| *A61B 90/00* | (2016.01) |
| *A61C 1/00* | (2006.01) |
| *A61C 7/08* | (2006.01) |
| *A61C 19/04* | (2006.01) |
| *A61C 19/05* | (2006.01) |

(52) U.S. Cl.
CPC .......... *A61B 5/0036* (2018.08); *A61B 5/1111* (2013.01); *A61B 5/4547* (2013.01); *A61B 5/4836* (2013.01); *A61B 5/682* (2013.01); *A61B 5/6843* (2013.01); *A61C 1/0015* (2013.01); *A61C 1/0038* (2013.01); *A61C 1/0061* (2013.01); *A61C 7/08* (2013.01); *A61C 19/04* (2013.01); *A61C 19/05* (2013.01); *A61B 1/00009* (2013.01); *A61B 2090/065* (2016.02); *A61B 2562/164* (2013.01); *A61B 2562/168* (2013.01); *A61C 7/006* (2013.01); *A61C 2204/005* (2013.01)

(58) Field of Classification Search
CPC .......... A61B 1/04; A61B 1/24; A61B 5/0002; A61B 5/1111; A61B 5/4547; A61B 5/4836; A61B 5/682; A61B 5/6843; A61B 2090/065; A61B 2562/164; A61B 2562/168
See application file for complete search history.

(56) References Cited

U.S. PATENT DOCUMENTS

| | | | |
|---|---|---|---|
| 4,823,788 | A | 4/1989 | Smith et al. |
| 7,819,661 | B2 | 10/2010 | Nadav |
| 10,806,376 | B2 | 10/2020 | Lotan et al. |
| 10,820,965 | B2 | 11/2020 | Lotan et al. |
| 10,874,483 | B2 * | 12/2020 | Boronkay ............... A61C 7/36 |
| 2002/0094509 | A1 | 7/2002 | Durbin et al. |
| 2007/0065768 | A1 | 3/2007 | Nadav |
| 2009/0017422 | A1 | 1/2009 | Creamer |
| 2009/0220921 | A1 | 9/2009 | Abolfathi et al. |
| 2012/0148976 | A1 | 6/2012 | Brawn |
| 2013/0040264 | A1 | 2/2013 | Scurtescu |
| 2015/0114439 | A1 | 4/2015 | Henderson et al. |
| 2015/0173856 | A1 | 6/2015 | Lowe et al. |
| 2015/0230885 | A1 | 8/2015 | Wucher |
| 2015/0305669 | A1 * | 10/2015 | Hultgren ............... A61C 19/05 433/215 |
| 2015/0314092 | A1 * | 11/2015 | Kimm ............... A61M 16/044 128/207.15 |
| 2016/0228212 | A1 | 8/2016 | Salah et al. |
| 2017/0028178 | A1 * | 2/2017 | Skoda ............... A61B 5/4064 |
| 2017/0251954 | A1 | 9/2017 | Lotan et al. |
| 2018/0078334 | A1 | 3/2018 | Lotan et al. |
| 2020/0405191 | A1 | 12/2020 | Lotan et al. |

FOREIGN PATENT DOCUMENTS

| | | |
|---|---|---|
| JP | 2014-131774 A | 7/2014 |
| WO | 2007/137302 A2 | 11/2007 |
| WO | 2015/040577 A1 | 3/2015 |
| WO | 2015/058284 A1 | 4/2015 |
| WO | 2017/149497 A3 | 10/2017 |
| WO | 2018/051303 A2 | 3/2018 |

OTHER PUBLICATIONS

Advisory Action received for U.S. Appl. No. 15/059,140, dated Nov. 29, 2019, 3 pages.
Applicant Initiated Interview Summary (PTOL-413) received for U.S. Appl. No. 15/269,465, dated May 14, 2019, 3 pages.
Authorized Officer: Bruckner, Benedikt, "Partial Search Report" dated Jul. 5, 2017 issued in corresponding PCT Application No. PCT/IB2017/051233.
Authorized Officer: Bruckner, Benedikt, Invitation to Pay Additional Fees in counterpart PCT application No. PCT/IB2017/051233, dated Apr. 5, 2017, 17 pp.
Communication dated Nov. 30, 2020 in related European Patent Application No. 17783584.0.
Ex Parte Quayle Action received for U.S. Appl. No. 15/059,140, mailed on Dec. 30, 2019, 4 pages.
"Final Office Action", U.S. Appl. No. 15/269,465, dated Mar. 19, 2018, 18 pp.
"Non-Final Office Action", U.S. Appl. No. 15/269,465, dated Jul. 28, 2017, 20 pp.
Examiner initiated interview summary received for U.S. Appl. No. 15/269,465, dated Mar. 20, 2020, 1 page.
"Non-Final Office Action", U.S. Appl. No. 15/059,140, dated Nov. 30, 2017, 6 pp.
Advisory Action issued in related U.S. Appl. No. 15/269,465, dated Jul. 26, 2018, 8 pp.
Final Office Action issued in related U.S. Appl. No. 15/269,465, dated Aug. 22, 2019, 20 pp.
Non-Final Office Action issued in related U.S. Appl. No. 15/269,465, dated Jan. 11, 2019, 20 pp.
Notice of Allowance issued in counterpart U.S. Appl. No. 15/269,465, dated Mar. 20, 2020, 14 pp.
Office Action (and English Translation) issued in counterpart Japanese patent application No. 2019-515331 dated Nov. 30, 2020.
Office Action issued in counterpart Japanese patent application No. 2018-565468, dated Nov. 2, 2020, 4 pp.
Final Rejection received for U.S. Appl. No. 15/059,140, dated Aug. 8, 2019, 8 pages.
Final Rejection received for U.S. Appl. No. 15/269,465, dated Aug. 22, 2019, 19 pages.
Non-Final Rejection received for U.S. Appl. No. 15/059,140, dated Jan. 14, 2019, 7 pages.
Non-Final Rejection received for U.S. Appl. No. 15/269,465, dated Jan. 11, 2019, 17 pages.
Notice of Allowance and Fees Due (PTOL-85) dated Aug. 24, 2020 for U.S. Appl. No. 15/059,140.
Notice of Allowance and Fees Due (PTOL-85) dated Jun. 29, 2020 for U.S. Appl. No. 15/269,465.
Notice of Allowance and Fees Due (PTOL-85) dated May 14, 2020 for U.S. Appl. No. 15/059,140.
Notice of Allowance and Fees Due (PTOL-85) dated Sep. 22, 2020 for U.S. Appl. No. 15/059,140.
Notice of Allowance received for U.S. Appl. No. 15/059,140, dated Jan. 27, 2020, 6 pages.
Notice of Allowance received for U.S. Appl. No. 15/269,465, dated Mar. 20, 2020, 13 pages.
Office Action issued in counterpart Korean patent application No. 10-2018-7028372, dated Mar. 2, 2020, 6 pp.
Office Action dated Jun. 1, 2020 in JP Patent Application No. 2018-565468.
Officer Benedikt Bruckner, "Invitation to Pay Additional Fees and, Where Applicable, Protest Fee", International Patent Application PCT/IB2017/051233, dated Jul. 5, 2017, 17 pp.
Officer Patricia Sanchez Gomez, "Invitation to Pay Additional Fees and, Where Applicable, Protest Fee", International Patent Application PCT/IB2017/055635, dated Dec. 20, 2017, 13 pp.
Officer: Bruce Fortune, "International Search Report and the Written Opinion", International Patent Application PCT/IB2017/051233, Completed Jun. 29, 2017, 23 pp.
Officer: Bruce Fortune, "International Search Report and the Written Opinion", International Patent Application PCT/IB2017/055635, Completed Dec. 5, 2017, 20 pp.
Office Action issued in counterpart European patent application No. 17716012.4, dated Oct. 13, 2019, 5 pp.
Controller of Patents: Aiswarya P N, Examination Report issued in Indian patent application No. 201927014905, dated Apr. 30, 2021, 5 pp.

(56) References Cited

OTHER PUBLICATIONS

Inventors: Tal Lotan et al., Orthodontic System With Tooth Movement and Position Measuring, Monitoring, and Control, Nov. 2, 2020, 44 pp.
Non-Final Rejection dated Oct. 14, 2022 for U.S. Appl. No. 17/021,914.
Office Action issued in counterpart Israeli patent application No. 261491, dated Aug. 29, 2021, 6 pp.
Office Action issued in counterpart Israeli patent application No. 261491, dated Dec. 7, 2021, 4 pp.
Patent Controller: Ritesh Kumar, Examination Report issued in counterpart Indian patent application No. 201827037049, dated May 21, 2021, 11 pp.
Shuiwei Xie, Examination Report issued in Australian patent application No. 2017328249, dated May 21, 2021, 3 pp., dated Jan. 11, 2023.
Examination Report issued in Australian patent application No. 2017225621, dated Mar. 12, 2021, 6 pp.
Examination Report issued in Australian patent application No. 2017225621, dated Sep. 16, 2021, 3 pp.
Office Action issued in Korean patent application No. 10-2018-7028372, dated Mar. 2, 2020, 6 pp. w/ translation.

* cited by examiner

ORTHODONTIC SYSTEM WITH TOOTH MOVEMENT AND POSITION MEASURING, MONITORING, AND CONTROL

CROSS-REFERENCE TO RELATED APPLICATIONS

This application is a divisional of U.S. patent application Ser. No. 15/269,465 filed on Sep. 19, 2016. The entire disclosure of U.S. patent application Ser. No. 15/269,465 is incorporated herein by reference.

FIELD

The present disclosure relates to orthodontics. More particularly, the present disclosure relates to an orthodontic system with tooth movement and position measuring, monitoring, and control during orthodontic treatment.

BACKGROUND

Malocclusion is an abnormal alignment of the teeth and is typically characterized by crooked, crowed, or protruding teeth and upper and lower teeth that do not fit together properly. Orthodontic treatment attempts to remedy malocclusion by properly aligning the teeth. One common orthodontic treatment uses an orthodontic appliance to properly align the teeth.

There are many known orthodontic appliances for aligning teeth. The most commonly known orthodontic appliance are braces, which are permanently fixed with respect to the teeth until treatment is completed. Braces typically include brackets that are bonded to individual teeth using a suitable adhesive, and wires that are threaded through or wrapped around a portion of each bracket. The wires apply a force against the teeth via the brackets, which gradually move the teeth into alignment.

In the last couple of decades, removable orthodontic appliances have been developed, which are worn part time or most of the time, day or night. These appliances fit in the intraoral cavity in a manner that allows them to apply a force against the teeth, which gradually move the teeth into alignment, and be easily removed from and refitted in the intraoral cavity by the patient. Such removable orthodontic appliances are described in U.S. Pat. No. 7,819,661 and U.S. patent application Ser. No. 15/059,140, the entire disclosures of which are incorporated herein by reference.

The amount and the duration of the force applied by the orthodontic appliance to the teeth must be controlled over the course of the orthodontic treatment to avoid undesirable effects, such as tooth root resorption and/or pain and discomfort associated with the orthodontic appliance.

Accordingly, an orthodontic system is needed with tooth movement and position measuring, monitoring, and control during orthodontic treatment.

SUMMARY

Disclosed herein are an orthodontic appliance for aligning at least one tooth of a patient's upper or lower jaw, and a system comprising at least one orthodontic appliance for aligning at least one tooth of the patient's upper jaw and/or at least one tooth of the patient's lower jaw. The orthodontic appliance may comprise a force exerting member for applying a force to move the at least one tooth, a tooth movement sensor member for obtaining tooth movement data, and a tooth movement monitor for calculating at least one of a distance the at least one of the tooth has moved and a current position of the at least one tooth from the tooth movement data.

Further disclosed herein is an electronic control console, which can be included in the system. The electronic control console can be operatively connected to the force exerting member and in data communication with the tooth movement monitor, for controlling the operation of the force exerting member using the least one of a distance the at least one of the tooth has moved and a current position of the at least one tooth.

In some embodiments, the orthodontic appliance may further comprise a mouthpiece.

In some embodiments, the force exerting member may be associated with the mouthpiece in a manner that allows physical engagement between the at least one force exerting member and the at least one tooth.

In some embodiments, the tooth movement sensor may be associated with the mouthpiece in a manner that allows physical engagement with the at least one tooth or optical communication with at least one of the at least one tooth.

In some embodiments, the force exerting member may comprise at least one inflatable element.

In some embodiments, the tooth movement sensor may comprise a mass flow sensor.

In some embodiments, the at least one inflatable element can be inflated with a fluid which causes the at least one inflatable element to apply and maintain the force applied to the at least one tooth and wherein the mass flow sensor measures the mass of the fluid used to expand the at least one inflatable element.

In some embodiments, the at least one inflatable element may comprise a plurality of inflatable elements and may further comprise a multiport solenoid valve or multiple solenoid valves connected with the inflatable elements, the multiport solenoid valve or multiple solenoid valves allowing the inflatable elements to be individually selected to measure the mass of the fluid used to inflate a selected one of the inflatable elements.

In some embodiments, at least a second tooth movement sensor can be provided which may be associated with the mouthpiece in a manner that allows physical engagement with the at least one tooth or optical communication with at least one of the at least one tooth.

In some embodiments, at least a second tooth movement sensor can be provided which may comprise at least one force sensor, at least one optical image sensor, or any combination thereof.

In some embodiments, the at least one force sensor may comprise at least one contact force sensor, at least one flexible force sensor, or any combination thereof, and the at least one optical sensor may comprise at least one micro video camera, at least one micro still camera, or any combination thereof.

In some embodiments, the at least one force sensor may measure at least one of a force applied thereto by the at least one tooth and a location of the applied force, and the at least one optical image sensor may obtain at least one optical image of at least one of the at least one tooth.

In some embodiments, the tooth movement monitor may comprise a controller for interrogating the tooth movement sensor member, and in response, receiving tooth movement data from the tooth movement sensor, the controller calculating the at least one of the distance the at least one tooth has moved and the current position of the at least one tooth from the tooth movement data.

In some embodiments, the electronic control console may comprise a fluid pump which causes the force exerting member to apply the force on the at least one tooth.

In some embodiments, the electronic control console may further comprise a controller for selectively controlling the operation of the fluid pump.

In some embodiments, the electronic control console may further comprise at least one fluid sensor and a valve for assisting the controller in selectively controlling the operation of the pump.

In some embodiments, the electronic control console may be programmable.

In some embodiments, the electronic control console and the tooth movement monitor may each comprise a communication interface, the communication interfaces allowing the data communication between the electronic control console and the tooth movement monitor.

In some embodiments, the communication interface of the electronic control console may allow data communication with a communication device operated by the patient, thereby allowing the at least one of the distance the at least one tooth has moved and the current position of the at least one tooth, whether in real time or stored, to be communicated by the communication device of the patient to a remotely located communication device of a remotely located dentist or other user.

In some embodiments, the communication interface of the electronic control console may allow receipt of program instructions from the remotely located communication device operated by the dentist or other user, via the communication device operated by the patient, the program instructions programming the controller of the control console.

In some embodiments, the communication interface of the electronic control console may allow receipt of program instructions from a remotely located communication device operated by a dentist or other user, the program instructions programming the controller of the control console.

In some embodiments, the communication interfaces of the electronic control console and the tooth movement monitor may allow a dentist or other user to remotely access the control console and the tooth movement monitor, via a communication device operated by the dentist and a communication device operated by the patient, to initiate a real time measurement of the at least one of the distance the at least one tooth has moved and the current position of the tooth, or obtain at least one of the distance the at least one tooth has moved and the current position of the tooth stored in the control console.

In some embodiments, the orthodontic system may further comprise a second orthodontic appliance, one of the first and second orthodontic appliances for aligning at least one tooth of the patient's upper jaw and the other one of the first and second orthodontic appliances for aligning at least one tooth of the patient's lower jaw.

Further disclosed herein is a method for aligning at least one tooth of a patient. The method comprising applying with a force exerting member a force to move the at least one tooth, obtaining with a tooth movement sensor member tooth movement data, calculating at least one of a distance the at least one tooth has moved and a current position of the at least one tooth from the tooth movement data obtained with the tooth movement sensor, and controlling the operation of the force exerting member with an electronic control console using the at least one of the distance the at least one tooth has moved and the current position of the at least one tooth.

In some embodiments, the obtaining may comprise interrogating the tooth movement sensor with a controller, and in response, receiving the tooth movement data obtained by the tooth movement sensor, the controller calculating the at least one of the distance the at least one tooth has moved and the current position of the at least one tooth from the tooth movement data.

In some embodiments, the method may further comprise sending, with a communication interface of the electronic control console, the at least one of the distance the at least one tooth has moved and the current position of the at least one tooth to a communication device of the patient.

In some embodiments, the method may further comprise sending, with the communication device of the patient, the received at least one of the distance the at least one tooth has moved and the current position of the at least one tooth to a remotely located communication device of a remotely located dentist or other user.

In some embodiments, the sending is performed in real time.

In some embodiments, the method may further comprise receiving, with the communication interface, program instructions from the remotely located communication device operated by the dentist or other user, the program instructions programming the controller of the control console.

In some embodiments, the method may further comprise initiating from a remotely located communication device operated by a dentist or other user, via the communication interface, a measurement of the at least one of the distance the at least one tooth has moved and the current position of the at least one tooth, or obtain the at least one of the distance the at least one tooth has moved and the current position of the at least one tooth stored in the controller.

DETAILED DESCRIPTION

Figure 1:
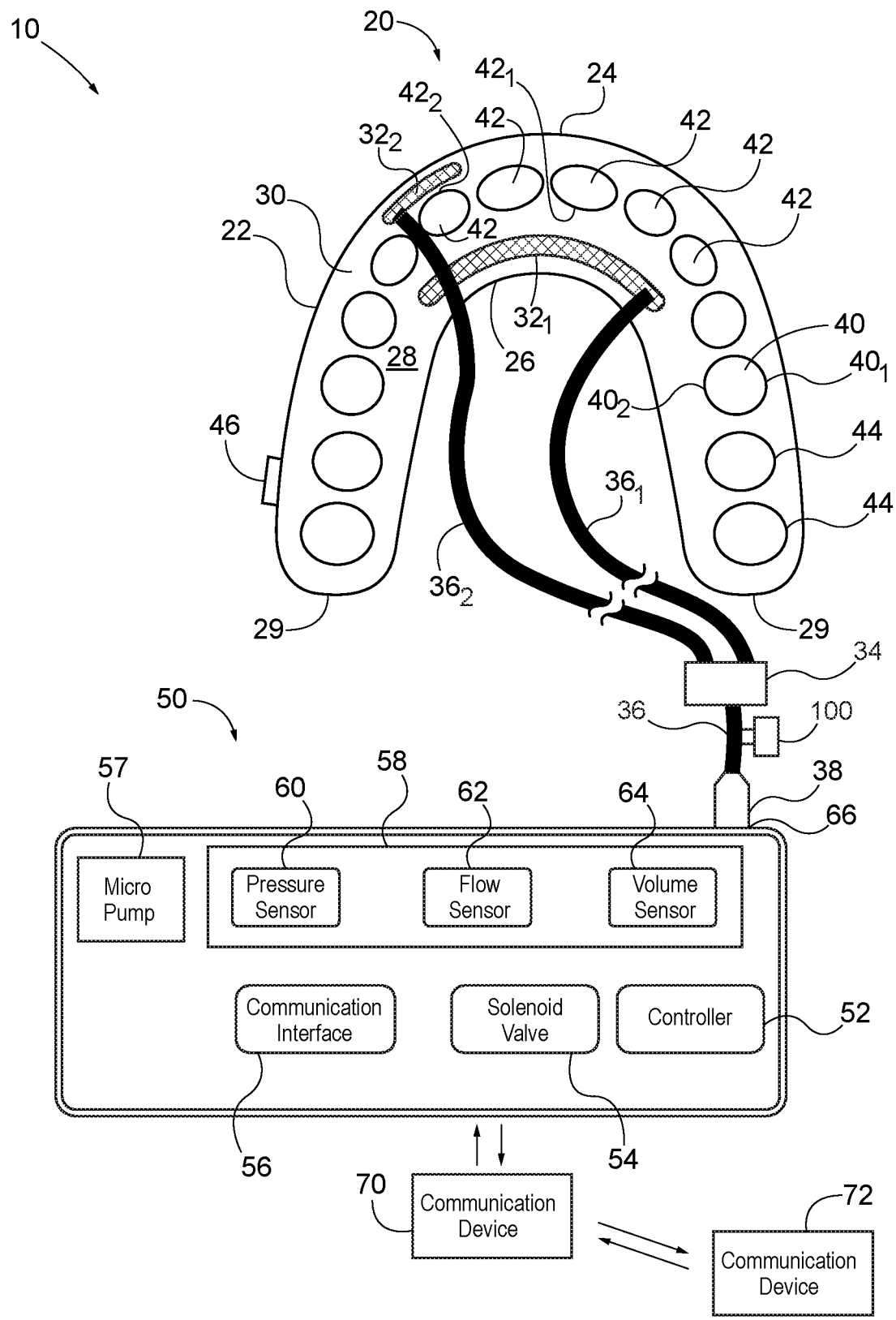
FIG. 1 is a schematic illustration of an orthodontics system according to an embodiment of the present disclosure.

FIG. 1 illustrates an embodiment of an orthodontics system 10 with tooth movement and position measuring, monitoring, and control during orthodontic treatment. The system 10 generally comprises at least one orthodontic appliance or aligner 20, which is configured to receive the teeth 40 of the upper or lower jaw of a patient, and a mobile programmable electronic control console 50.

The aligner 20 of the system 10 moves and aligns each tooth 42 requiring alignment, along a predetermined three-dimensional path under the control of the control console 50. The teeth 42 requiring alignment may be adjacent to one another, spaced one from another, arranged in groups, or be all the teeth in the same arch of the intraoral cavity. The aligner 20 can be configured to move one or more of the teeth 42 requiring alignment in a lingual direction L and/or in a buccal/labial direction B.

As illustrated in FIG. 1, the aligner 20 may comprise a generally U-shaped mouthpiece 22, one or more inflatable elements (two inflatable elements $32_1$, $32_2$ are shown for illustrative purposes only) and a tooth movement monitor 46. The mouthpiece 22 of the aligner 20 may include a channel 30 formed by a curved labial/buccal (facial) wall 24, a curved lingual wall 26, an incisal/occlusal (base) wall 28 connecting the facial wall 24 and lingual wall 26, and posterior walls 29 connecting posterior ends of the facial wall 24 and lingual wall 26. The mouthpiece 22 can be made from a transparent, semi-transparent or opaque dental-compatible material, which may be rigid or at least sufficiently rigid to ensure that the mouthpiece 22 does not deform under tooth aligning forces. Suitable materials for the mouthpiece 22 include, without limitation, thermoplastic polycarbonate, acrylic resin, and like materials.

Referring still to FIG. 1, the channel 30 of the mouthpiece 22 is configured to receive teeth 40 of a patient's upper or lower jaw. The facial wall 24 and the lingual wall 26 both extend along the facial and lingual surfaces $40_1$ and $40_2$, respectively, of the teeth 40 of the dental arch of the jaw, and the base wall 28 extends along the incising edges $40_3$ of the teeth 40 (FIG. 2) when the mouthpiece 22 is inserted into the mouth. In some embodiments, where the facial wall 24 and lingual wall 26 are connected to the base wall 28, the posterior walls 29 can be omitted so that the ends of the channel 30 are open. Such embodiments may be useful where it is desirable to reduce the length of the facial and lingual walls 24 and 26, so that they do not extend past certain teeth 44 not requiring alignment, such as the second and/or third molars or other teeth 44 of the dental arch.

The inflatable elements $32_1$, $32_2$ illustrated in FIG. 1 are configured to apply a force to one or more teeth 42 requiring alignment, when inflated with a suitable fluid. Such fluid may include, without limitation, a gas such as air, a liquid such as water, or any other suitable fluid. The inflatable elements $32_1$, $32_2$ can comprise inflatable sleeves, balloons, or other devices that can be inflated and expanded with a fluid. The inflatable elements $32_1$, $32_2$ can be attached to or partially embedded in the inner surface of the facial wall 24 and/or the lingual wall 26, and/or base wall 28 of the mouthpiece 22. A branch fluid conduit or tube $36_1$, $36_2$ may extend from each inflatable element $32_1$, $32_2$ to allow fluid connection thereof to the programmable electronic control console 50, which is configured to selectively inflate and deflate the inflatable elements $32_1$, $32_2$ with the fluid. Typically, the inflatable elements $32_1$, $32_2$ when deflated, do not exert a force against the teeth 42 requiring alignment and may or may not make contact therewith. When inflated, the inflatable elements $32_1$, $32_2$ expand and contact the teeth 42 requiring alignment, thereby applying a force which urges the teeth 42 in the desired predetermined three-dimensional path.

Referring still to FIG. 1, the inflatable elements $32_1$, $32_2$ are selectively disposed within the mouthpiece 22 so that they apply a force to the one or more teeth 42 requiring alignment in a manner which moves each tooth 42 along a three-dimensional path that has been predetermined to be suitable for that particular tooth 42. As illustrated in FIG. 1, one of the inflatable elements $32_1$ can be provided between multiple teeth 42 requiring alignment and the lingual wall 26 of the mouthpiece 22, so that it exerts a force on the lingual surface $42_1$ of these teeth 42. The other inflatable element $32_2$ can be located between another tooth 42 requiring alignment and the facial wall 24 of the mouthpiece 22, so that it exerts a force on the facial surface $42_2$ of that tooth 42. The aligner can be provided with any combination of single and/or multiple tooth inflatable elements, depending upon the orthodontic correction that is needed. All the inflatable elements may be located on the same side (lingual or facial) of the teeth requiring alignment or on opposite sides thereof as illustrated in FIG. 1.

Still referring to FIG. 1, the tooth movement monitor 46 can be disposed on an outer surface of the mouthpiece 22. In other embodiments of the aligner, the tooth movement monitor 46 can be partially embedded in the outer surface of the mouthpiece 22. In still other embodiments, the tooth movement monitor 46 can be fully embedded in the mouth piece 22.

Figure 3:
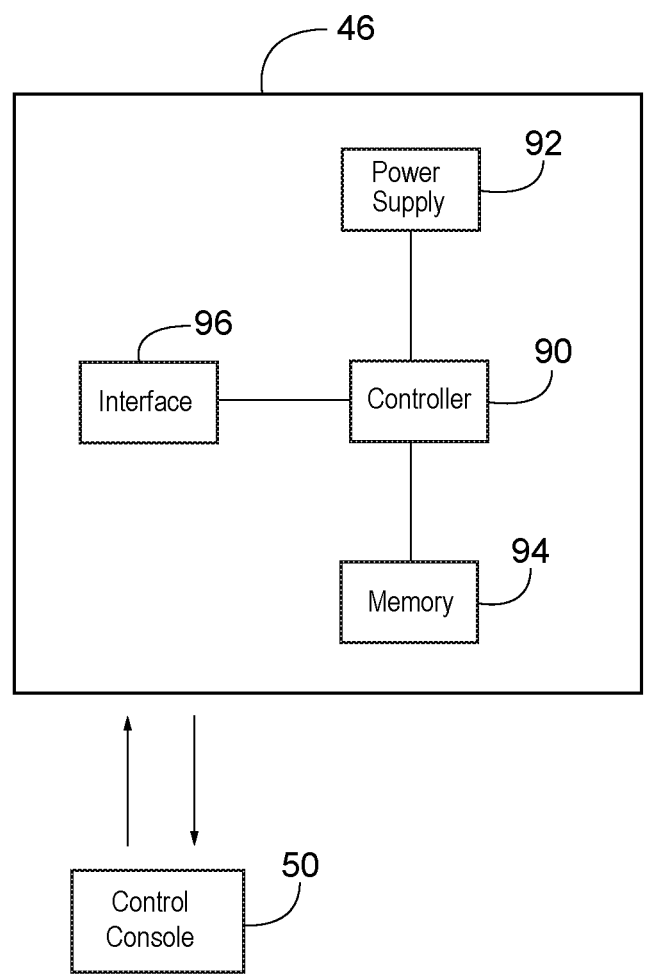
FIG. 3 is a block diagram of an embodiment of a tooth movement monitor.

Referring now to FIG. 3, the tooth movement monitor 46 can include a controller 90, a power supply 92 connected to the controller 90, and a memory 94 connected to the controller 90. The controller 90 receives input from a mass flow sensor 100 (FIG. 1), which measures the mass of the fluid (e.g., air or water) that has been pumped into the one or more inflatable elements to apply and maintain the force on the one or more teeth 42 requiring alignment, as will be explained further on in more detail. The tooth movement monitor 46 can further include a communication interface 96 connected to the controller 90, which allows the tooth movement monitor 46 to communicate with the programmable electronic control console 50. The controller 90 of the tooth movement monitor 46 may comprise without limitation a microcontroller, microprocessor, application specific integrated circuit (ASIC), or field programmable gate array (FPGA).

Figure 2:
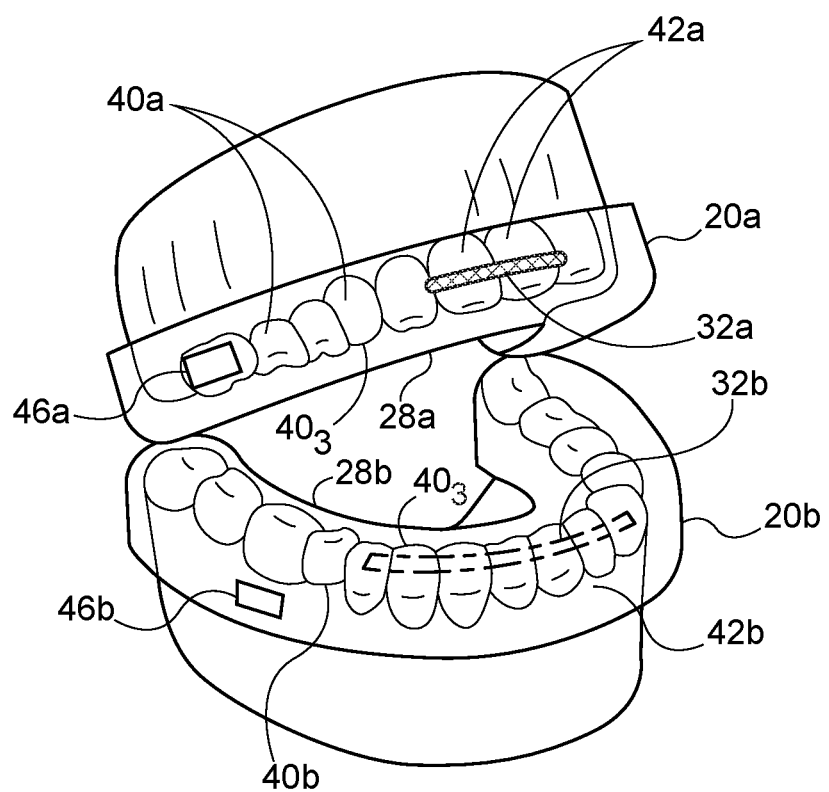
FIG. 2 illustrates an embodiment of the system (the mobile programmable electronic control console not shown) comprising a first or upper aligner for aligning the teeth of the upper jaw of the patient and a second or lower aligner for aligning the teeth of the lower jaw of the patient, where each aligner comprises a mass flow sensor (not shown) which is operative as a tooth movement sensor.

FIG. 2 illustrates another embodiment of the system (the mobile programmable electronic control console not shown) which comprises two of the above-described aligners, i.e., a first aligner $20_a$, which receives the teeth 40 of the upper jaw of the patient and a second aligner $20_b$, which receives the teeth 40 of the lower jaw of the patient. The aligner(s) $20_a$, $20_b$ are configured to move and thereby align one or more teeth $42_a$, $42_b$ of the upper and lower jaws of the patient. The aligners $20_a$, $20_b$ can respectively include one or more inflatable elements $32_a$, $32_b$ and tooth movement monitors $46_a$, $46_b$. In other embodiments, just one of the aligners may be provided with the tooth movement monitor. In such embodiments, the single tooth movement monitor would receive mass fluid flow measurements obtained by the mass flow sensors associated with each aligner.

Referring again to FIG. 1, the programmable electronic control console 50 of the system 10 can comprise a fluid micro pump 57, a fluid sensor arrangement 58, a solenoid valve 54, a controller 52 for controlling the operation of the micro pump 57, and a communication interface 56. The micro pump 57 of the control console 50 can be connected to the one or more inflatable elements $32_1$, $32_2$ of the aligner 20 via their branch fluid tubes $36_1$, $36_2$, main fluid tube 36, and multiport solenoid valve or multiple solenoid valves 34, so that it can inflate and expand the inflatable elements $32_1$, $32_2$ with the fluid. A connector 38 can be provided at the free end of the main fluid tube 36 so it can be removably connected to an outlet 66 of the micro pump 57 located externally on the control console 50. The solenoid valve 54 of the control console 50 can be configured to allow the patient, doctor and/or other end user to adjust the fluid pressure of the micro pump 57 and release the fluid pressure to deflate the one or more inflatable elements 32, prior to disconnecting the fluid tube 36 from the control console 50.

The micro pump 57 of the control console 50 can comprise a piezoelectric micro pump, an electrostatic micro pump, a pneumatic micro pump, a linear pump, a syringe pump, or any other suitable pump that is capable of inflating the one or more inflatable elements 32 with any of the fluids mentioned above (e.g., air, water, etc.) and which is capable of being contained within the mobile control console 50.

The controller 52 of the control console 50 can comprise any suitable microcontroller which is capable of selectively controlling the operation of the micro pump 57 so that the force exerted by the inflatable elements $32_1$, $32_2$ on the teeth 42 requiring alignment, may be constant, varied, or a combination thereof. The controller 52 is configured to be programed locally or remotely by a dentist, dental technician, and/or patient. The inflatable elements $32_1$, $32_2$ can be made to exert a constant force of a desired magnitude on the teeth 42 requiring alignment by programming the controller 52 to energize the micro pump 57 so that it inflates to a pressure which expands the inflatable elements $32_1$, $32_2$ and causes them to exert and maintain the desired force, as the teeth 42 requiring alignment move along their predetermined three-dimensional path.

The controller 52 of the console 50 can also be programmed to selectively operate the micro pump 57 and the solenoid valve 54, such that the micro pump 57 inflates and expands the inflatable elements $32_1$, $32_2$ and the solenoid valve 54 deflates and contracts the inflatable elements $32_1$, $32_2$ in manner that causes them to exert a varied force on the teeth 42 requiring alignment, for example, in the form of periodic pulses, which provide a pulsating force to the teeth requiring alignment 42. When so programmed, the controller 52 cyclically (at a desired frequency selected by the dentist or dental technician) energizes and de-energizes the micro pump 57 and solenoid valve 54 at the appropriate times, so that the micro pump 57 inflates and expands the inflatable elements $32_1$, $32_2$ thereby causing them to exert the desired force for a certain time period on the teeth 42 requiring alignment, and then de-energizes the micro pump 57 and opens the solenoid valve 54 for a certain time period, to release the fluid pressure and deflate the inflatable elements $32_1$, $32_2$.

The controller 52 of the console 50 can be programmed by the dentist or dental technician to stop the operation of the micro pump 57 and open the solenoid valve 54 to terminate the force exerted by the inflatable elements $32_1$, $32_2$ on the teeth 42 requiring alignment, when they arrive at their final positions. The controller 52 of the control console 50 can store tooth movement and/or position data obtained by tooth movement monitor 46 of each the aligner 20 of the system 10. The control console controller 52 may comprise but is not limited to a microcontroller, a microprocessor with external memories or a field programmable gate array (FPGA).

Referring still to FIG. 1, the fluid sensor arrangement 58 of the control console 50 provides the controller 52 with micro pump performance data, which can be used by the controller 52 to selectively control the operation of the micro pump 57. The fluid sensor arrangement 58 can comprise a fluid pressure sensor 60, a fluid flow sensor 62, and fluid volume sensor 64. The fluid pressure sensor 60 detects the fluid pressure of the micro pump 57, the fluid flow sensor 62 measures the fluid flow rate of the micro pump 57, and the fluid volume sensor 64 measures the fluid volume of the micro pump 57. The fluid pressure, flow, and volume measurements can be used by the controller 52 of the console 50 to control the energizing and the speed of the pump, so that the micro pump 57 maintains a desired inflation pressure and corresponding tooth moving forces.

The console communication interface 56 of the control console 50 can be configured to receive tooth movement and/or position data obtained with tooth movement monitor 46, as will be explained further on.

Figure 4A:
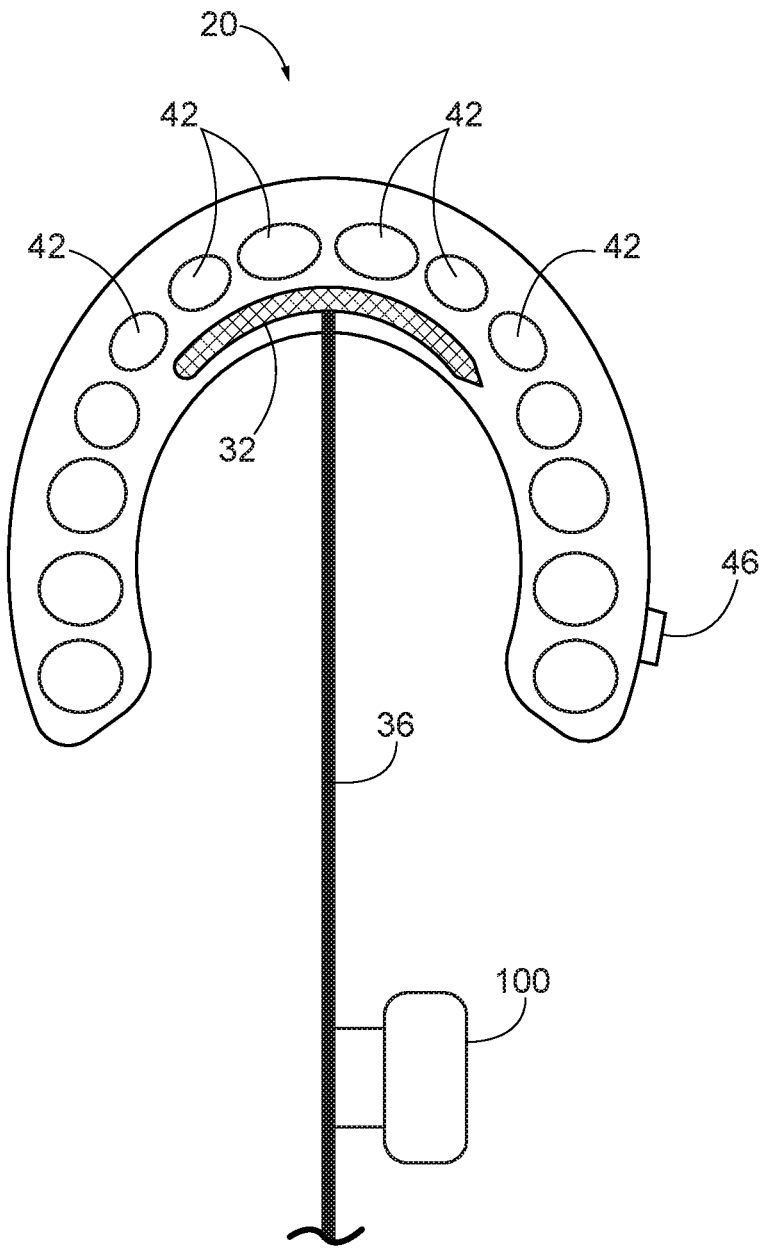
FIG. 4A is a schematic illustration of an embodiment of the aligner comprising a mass flow sensor which is operative as tooth movement sensor with an inflatable element.
Figure 4B:
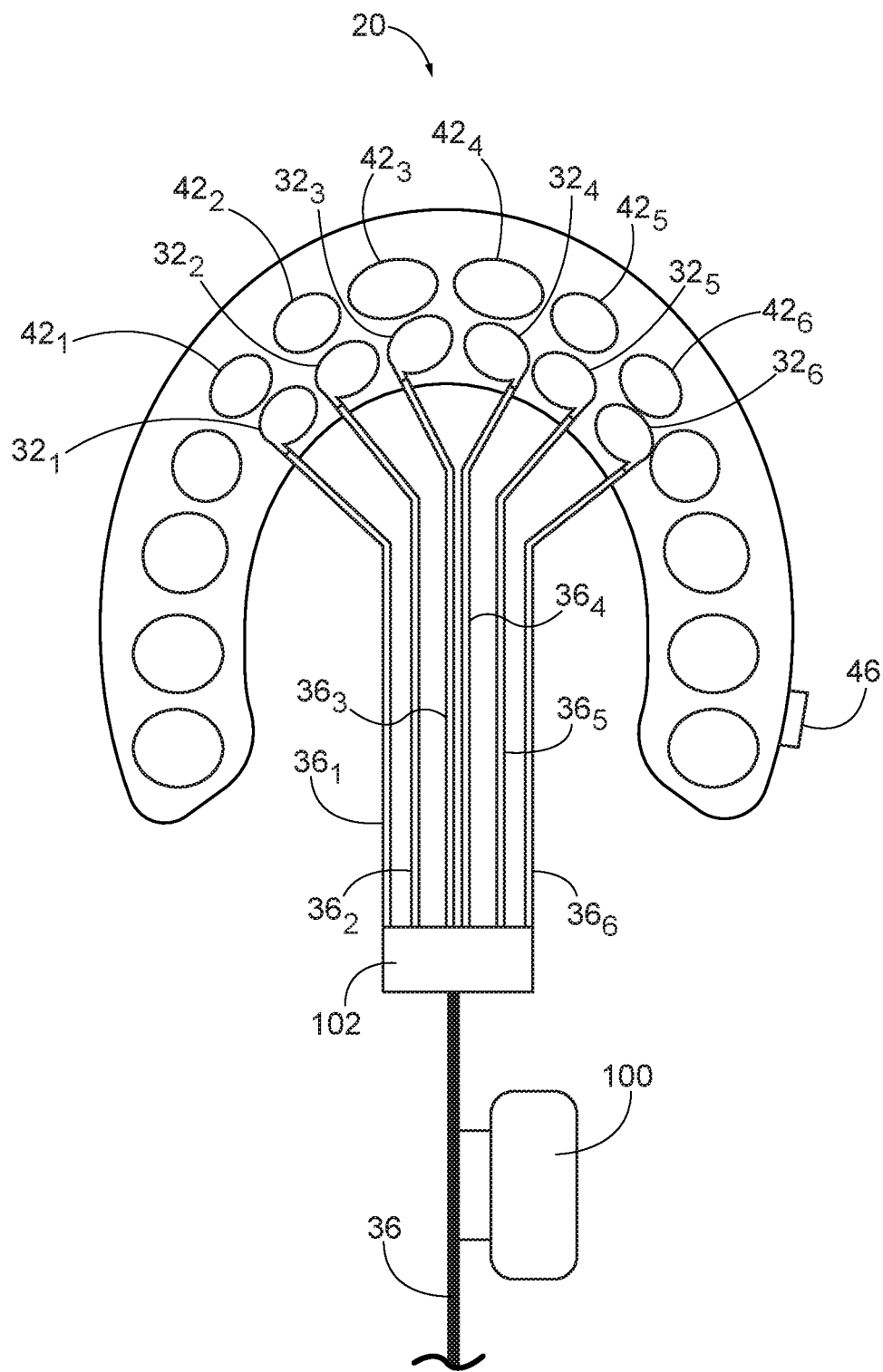
FIG. 4B is a schematic illustration of another embodiment of the aligner comprising a mass flow sensor which is operative as tooth movement sensor with multiple inflatable elements.

Referring now to FIGS. 4A and 4B, the mass flow sensor 100 of the aligner 20 operates as a tooth movement sensor by measuring the mass of fluid used to inflate the inflatable element 32 (FIG. 4A) or inflatable elements $32_{1-6}$ (FIG. 4B). The mass fluid flow measurements can then be communicated to the tooth movement monitor 46, which uses the measurements to determine tooth movement and/or tooth position in real time and/or the amount of tooth movement and/or the tooth position since a previous tooth movement and/or tooth position calculation. The mass flow sensor 100 measures the mass of the first volume of fluid used to inflate the inflatable element 32 or elements $32_{1-6}$ to a pressure which causes the inflatable element 32 or inflatable elements $32_{1-6}$ to apply a force which will move the teeth 42, $42_{1-6}$ requiring alignment along the desired path to proper alignment. As the teeth 42, $42_{1-6}$ move, the inflatable element 32 or inflatable elements $32_{1-6}$ is/are inflated with additional volumes of fluid to maintain the pressure therein, and thereby maintain the force applied to the teeth 42, $42_{1-6}$. The additional volumes of fluid provide corresponding increases in the size (volume) of the inflatable element 32, or inflatable elements $32_{1-6}$. The increases in size or volume of the inflatable element 32, or inflatable elements $32_{1-6}$ is/are, in turn, used by the tooth movement monitor 46 to determine the position and/or distance the teeth 42, $42_{1-6}$ have moved.

As illustrated in FIGS. 4A and 4B, the mass flow sensor 100 can be serially or shunt connected with the main fluid tube 36 to measure the mass of fluid (gas or liquid) pumped into the inflatable element 32 or each of the inflatable elements $32_{1-6}$. The mass flow sensor 100 can be configured to transmit the mass fluid flow measurements to the tooth movement monitor 46, which uses the mass fluid flow measurements to calculate tooth position and/or tooth movement. Embodiments of the aligner having multiple inflatable elements $32_{1-6}$, such as illustrated in FIG. 4B, can include a multiport solenoid valve or multiple solenoid valves 102 and individual fluid tubes $36_{1-6}$, fluidly connecting respective ones of the multiple inflatable elements $32_{1-6}$ with the main fluid tube 36. The solenoid valve or valves 102 can be operated to allow fluid communication between the main fluid tube 36 and a selected one of the individual fluid tubes $36_{1-6}$, so that the mass flow sensor 100 can measure the mass of fluid pumped into the selected inflatable element $32_{1-6}$. In other embodiments, a mass flow sensor can be connected with each of the individual fluid tubes to measure the mass fluid flow into its respective inflatable element $32_{1-6}$. In still other embodiments, the main fluid tube can be omitted and each individual fluid tube can be directly connected to the control console. In such embodiments, a mass flow sensor can be connected with each of the individual fluid tubes to measure the mass fluid flow into its respective inflatable element $32_{1-6}$.

The tooth movement monitor 46, via the controller 90, can be configured to interrogate the mass flow sensor 100, and in response, receive mass fluid flow measurements obtained by the mass flow sensor 100. The controller 90 of the tooth movement monitor 46 can then use the mass fluid flow measurements to calculate in real time the volume (increase) of the inflatable element 32 or inflatable elements $32_{1-6}$ and therefore, the amount each tooth 42 requiring alignment has moved and/or the current position of the tooth and/or determine the current position of and/or the amount each tooth 42 requiring alignment has moved relative to a previously calculated tooth position stored in the memory by the monitor 46. In some embodiments, 3D files representing the pretreatment position of the teeth and the Setup (final position of the teeth) are obtained for use in manufacturing the mouthpiece 22 for a patient. Any sub-step between the pretreatment position and the Setup can then be derived, as described above with the tooth movement monitor 46. The calculation performed by the controller 90 of the monitor 46 can be based on the volume change of the one or more inflatable elements 32.

The communication interface 96 of the tooth movement monitor 46 (FIG. 3) and the communication interface 56 of the programmable electronic control console 50 (FIG. 1), can be configured to communicate with one another via a wired, wireless, or optical connection. This allows the tooth movement monitor 46 to send tooth movement and position data to the control console 50. In addition, the two-way communication between the tooth movement monitor 46 and the control console 50 allows a dentist or other dental technician to use the control console 50 to obtain real time tooth movement and/or position measurement via the tooth movement monitor 46. The wireless communication can be implemented using any suitable radio frequency (RF) method including but not limited to Bluetooth®, wireless fidelity (Wi-Fi), near field communication (NFC), and/or radio frequency identification (RFID). Optical communication can be implemented using any suitable optical communication method such as, but not limited to infrared (IR).

The control console communication interface 56, in some embodiments, may be further configured to communicate with a communication device 70 used by a patient, which may include, without limitation, a hand-held mobile device such as a smartphone, a tablet computer, and/or a personal computer, via the wired, RF and/or optical methods described earlier. The communication device 70 can be communicatively connected to a cellular network, such as a mobile phone network, and/or a computer network, such as the Internet. The computer network can be a local server or personal computer or a network of remote servers hosted on the internet (e.g., cloud computing arrangement). So configured, the console communication interface 56 allows the control console 50 to send real time or stored tooth movement and/or position data (stored in the controller 52 of the control console 50 and/or the controller 90 of the tooth movement monitor 46), via the patient's communication device 70, to a communication device 72 used by a remotely located dentist or dental technician. The communication device 72 used by the dentist or dental technician may include, without limitation, a hand-held mobile device, such as a smartphone, a tablet computer, and/or a personal computer. The dentist or dental technician, in turn, may then use the communication device 72 to send a new program to the controller 52 of the control console 50, via the patient's communication device, from the remote location, in response to the tooth movement data received from the control console 50. In addition, the dentist or dental technician can remotely access the control console 50, via communication devices 70 and 72, and initiate a real time measurement of tooth movement and position via the tooth position monitor 46 and control console, or obtain tooth movement and position data stored in the control console 50.

Figure 5A:
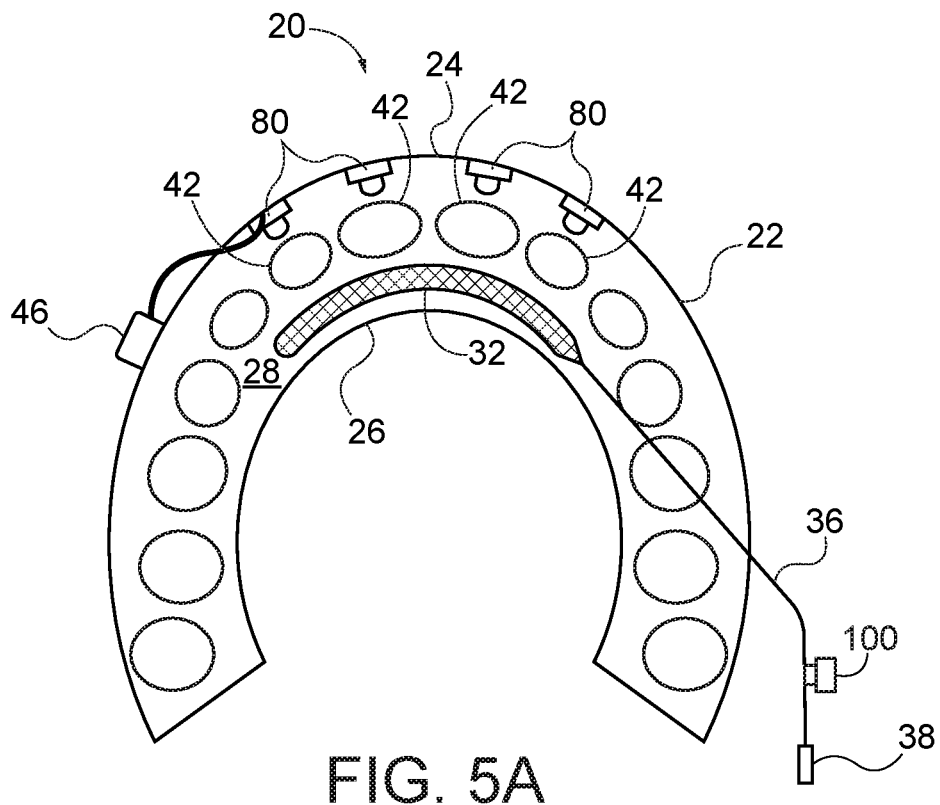
FIG. 5A is a schematic illustration of another embodiment of the aligner comprising a mass flow sensor and one or more contact force sensors, which can be used together or separately as tooth movement sensors.

In some embodiments of the system, the mass fluid flow measurements obtained with the mass flow sensor can be combined with additional tooth movement and/or tooth position measurement methods. For example, FIG. 5A illustrates an embodiment comprising an aligner 120, which is similar to the aligners described earlier and illustrated in any of FIGS. 1, 2, 4A, and 4B, however, the aligner 120 further includes one or more additional tooth movement sensors which take the form of contact force sensors 80. The contact force sensors are arranged within the mouthpiece 22 of the aligner 120 so that each force sensor 80 is adjacent to a tooth 42 requiring alignment. When the force sensor 80 is engaged by a tooth 42 moved by the inflatable element 32, the sensor 80 measures the amount of force exerted by the tooth 42 and generates a signal (wired, wireless, or optical) representing the measured amount of force. The tooth movement monitor 46 can then selectively use the mass fluid flow measurements, the force measurements, or both the mass fluid flow and force measurements to calculate the amount of tooth movement and/or position of each tooth 42 in real time and/or the amount of tooth movement and/or the position of each tooth 42 since a previous tooth movement and/or tooth position calculation. The one or more force sensors 80 may each comprise a pressure sensor, such as, but not limited to a piezoresistive force sensor, a strain gauge, a load cell, or any other suitable pressure sensor. The one or more contact force sensors 80 can be attached to or partially embedded in the interior surface of the facial wall 24 and/or the lingual wall 26 and/or the base wall 28 of the mouthpiece 22, such that each sensor 80 contacts the side of the tooth 42, which is opposite the inflatable element 32.

Figure 5B:
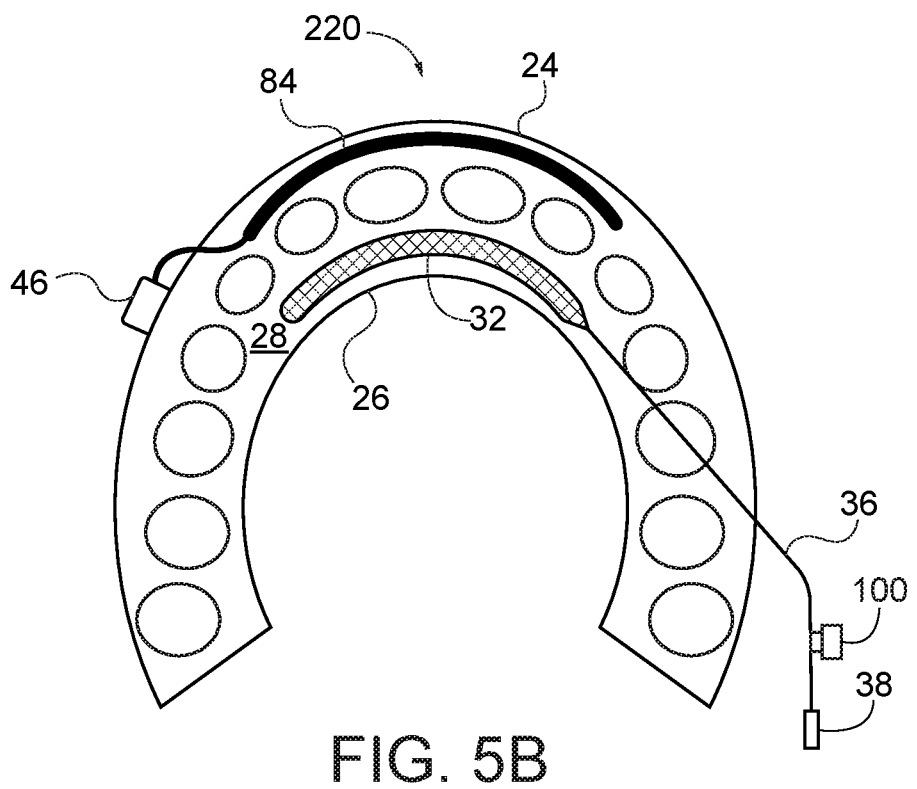
FIG. 5B is a schematic illustration of another embodiment of the aligner comprising a mass flow sensor and one or more flexible force sensors, which can be used together or separately as tooth movement sensors.

FIG. 5B illustrates another embodiment the system comprising an aligner 220 similar to the aligners described earlier and illustrated in any of FIGS. 1, 2, 4A, and 4B, however, the aligner 220 further comprises one or more flexible force sensors 84 arranged within the mouthpiece 22 of the aligner 20 adjacent to one or more teeth 42 requiring alignment, which are operative as tooth movement sensors. When the flexible force sensor 84 is engaged by one or more of the teeth 42 moved by the inflatable element 32, the sensor 84 measures an input representing the measured amount of force and the location applied by each tooth 42 on the flexible force sensor 84. The tooth movement monitor 46 can then selectively use the mass fluid flow measurements, the force measurements, or both the mass fluid flow and force measurements to calculate the amount of tooth movement and/or position of each tooth 42 in real time and/or the amount of tooth movement and/or the position of each tooth 42 since a previous tooth movement and/or tooth position calculation. Each of the one or more flexible force sensors 84 may comprise a FlexiForce® force sensor marketed and sold by Tekscan®, a FSR 400 Force Sensing Resistor® marketed and sold by Interlink Electronics®, a K90cN force sensor marketed and sold by Faraday-Sensoren, a S8-1N SingleTact force sensor marketed and sold by Pressure Profile Systems, Inc. or a HSFPAR003A force sensor marketed and sold by ALPS Electric Co., LTD. The one or more flexible force sensors 84 can be attached to or embedded in the interior surface of the facial wall 24 and/or the lingual wall 26 and/or the base wall 28 of the mouthpiece 22, such that each sensor 84 contacts the side of the tooth 42, which is opposite the one or more inflatable element 32.

Figure 5C:
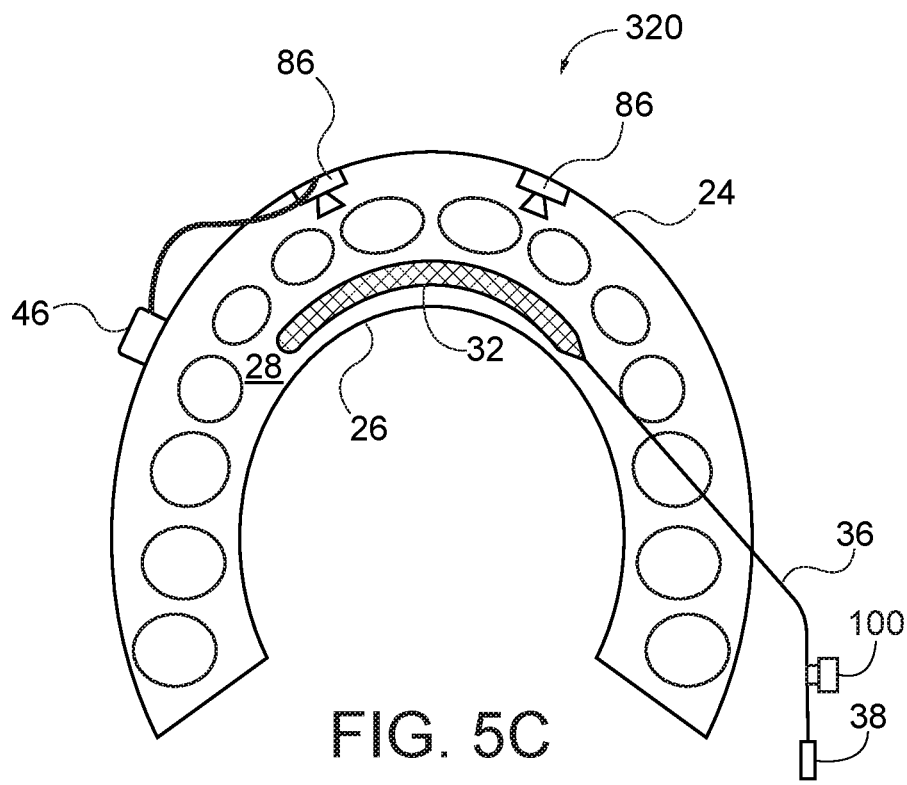
FIG. 5C is a schematic illustration of another embodiment of the aligner comprising a mass flow sensor and one or more optical image sensors, which can be used together or separately as tooth movement sensors.

FIG. 5C illustrates still another embodiment of the system comprising an aligner 320 similar to the aligners described earlier and illustrated in any of FIGS. 1, 2, 4A, and 4B, except that the aligner 320 further comprises one or more optical image sensors 86 arranged within the mouthpiece 22, which capture optical images of the position of at least the one or more teeth 42 requiring alignment, and thus operate as tooth movement sensors. Each optical image sensor 86 generates a signal (wired, wireless, or optical) representing the captured optical image (video or still), which can be used to calculate the movement and position of each tooth in the image in real time or the amount of movement since a previously calculated tooth position. The tooth movement monitor 46 can selectively use the mass fluid flow measurements, the captured optical images, or both the mass fluid flow measurements and the captured optical images, to calculate the amount of tooth movement and/or position of the teeth 42 in real time and/or the amount of tooth movement and/or the position of the teeth 42 since a previous tooth movement and/or tooth position calculation. Each of the image sensors 86 may comprise, without limitation, a micro video camera, a micro still camera, or any other suitable image sensor, which can be unobtrusively integrated within the mouthpiece 22 of the aligner 320 and can convert optical images into signals (wired, wireless, or optical). The one or more optical image sensors can be attached to or embedded in the inner surface of the facial wall 24 and/or the lingual wall 26 and/or the base wall 28 of the mouthpiece 22, such that each sensor can obtain an optical image of at least the one or more teeth 42 requiring alignment.

Figure 5D:
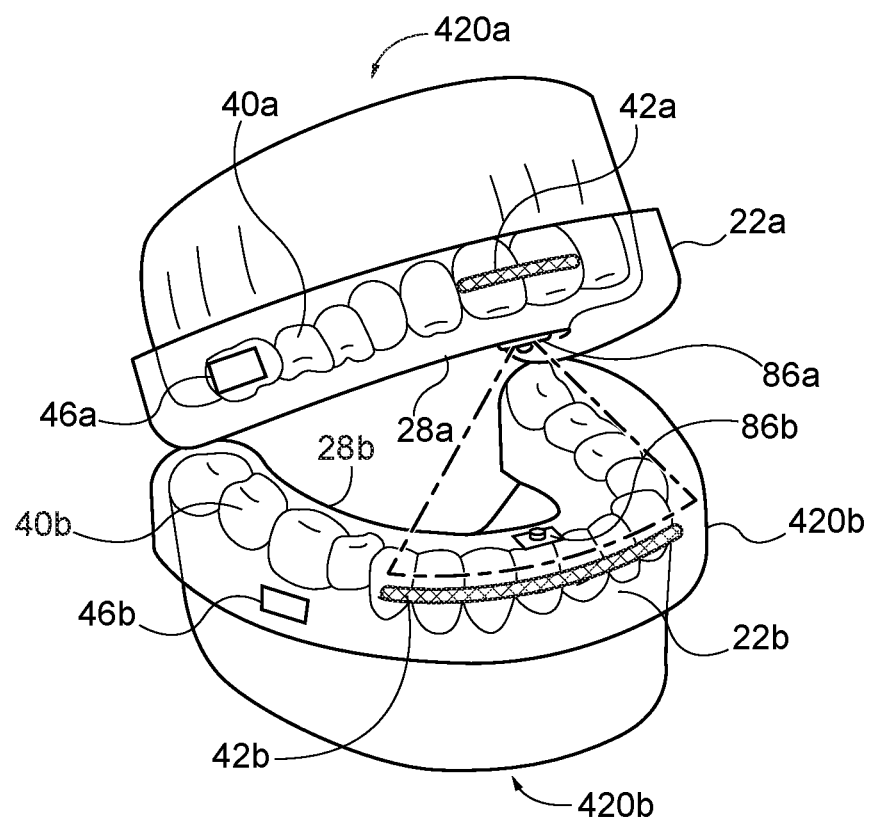
FIG. 5D illustrates another embodiment of the system (the mobile programmable electronic control console not shown) which comprises a first aligner for aligning the teeth of the upper jaw of the patient and a second aligner for aligning the teeth of the lower jaw of the patient. Each of the aligners comprises a mass flow sensor and one or more optical image sensors, which can be used together or separately as tooth movement sensors.

FIG. 5D illustrates yet another embodiment of the system comprising a first aligner 420$_a$ (transparent in this embodiment), which aligns one or more teeth 42 requiring alignment of the upper jaw and a second aligner 420$_b$ (transparent in this embodiment), which aligns one or more teeth 42b requiring alignment of the lower jaw. The aligners 420$_a$, 420$_b$ are also similar to the aligners described earlier and illustrated in any of FIGS. 1, 2, 4A, and 4B, however, the first aligner 420$_a$ can further comprise at least a first optical image sensor 86$_a$, which is operative as a tooth position sensor and can be attached to or partially embedded in an exterior surface of the base wall 28a of the first aligner's mouthpiece 22 (or fully embedded in the base wall 28). The first optical image sensor(s) 86$_a$ can capture an optical image of the position of at least the one or more teeth 42b requiring alignment of the opposite lower jaw, through the transparent second aligner 420$_b$. The second aligner 420$_b$ can further comprise at least a second optical image sensor 86$_b$, which is also operative as a tooth movement sensor and can be attached to or partially embedded in an exterior surface of the base wall 28b of the second aligner's mouthpiece 22b (or fully embedded in the base wall 28b). The second optical image sensor(s) 86$_b$ can capture an optical image of the position of at least the one or more teeth 42a requiring alignment of the opposite upper jaw, through the transparent first aligner 420$_a$. The optical image sensors 86$_a$, 86$_b$ generate signals (wired, wireless, or optical) representing the captured optical images (video or still), which can be used by the tooth movement monitors 46$_a$, 46$_b$ to calculate the movement and position of each tooth 42a, 42b in real time or the amount of tooth movement since a previously calculated tooth position. The tooth movement monitors 46$_a$, 46$_b$ can selectively use the mass fluid flow measurements, the captured optical images, or both the mass fluid flow measurement and the captured optical images, to calculate the amount of tooth movement and/or position of each tooth 42a, 42b in real time and/or the amount of tooth movement and/or the position of each tooth 42a, 42b since a previous tooth movement and/or tooth position calculation. Each of the optical image sensors 86$_a$, 86$_b$ may comprise, without limitation, a micro video camera, a micro still camera or any other suitable image sensor, which can be unobtrusively integrated within the mouthpiece 22a, 22b of the aligner 420$_a$, 420$_b$ and can convert optical images into signals (wired, wireless, or optical).

In other embodiments, the system can include the mass flow sensor and one or more of the one or more contact force sensors 80, one or more flexible force sensors 84, and one or more of the optical image sensors 86, 86$_a$, 86$_b$. The contact force sensors 80, flexible force sensors 84, and optical image sensors 86, 86$_a$, 86$_b$ can be communicatively connected (e.g., wired, wireless, or optically) to or with their associated tooth movement monitors. The wireless connection can be implemented using any suitable radio frequency (RF) method including but not limited to Bluetooth®, wireless fidelity (Wi-Fi), and/or radio frequency identification (RFID). Optical connections can be implemented using any suitable optical communication method such as, but not limited to infrared (IR).

Although the orthodontic system, its individual components, and their corresponding methods of operation and use have been described in terms of illustrative embodiments, they are not limited thereto. Rather, the appended claims should be construed broadly to comprise other variants and embodiments of the orthodontic system, its individual components, and their corresponding methods of operation and use, which may be made by those skilled in the art without departing from the scope and range of equivalents of the same.

What is claimed is:

1. An electronic control console for controlling the operation of at least one orthodontic appliance which moves and aligns at least one tooth of at least one jaw of a patient, the electronic control console comprising:

a fluid pump which causes a force exerting member of the at least one orthodontic appliance to apply a force on the at least one tooth, the force exerting member comprising at least one inflatable element that is inflatable with a fluid which causes the at least one inflatable element to apply and maintain the force applied to the at least one tooth;

a fluid sensor arrangement, a solenoid valve, a controller, and a communication interface, the fluid sensor arrangement including a fluid pressure sensor, a fluid flow sensor, and fluid volume sensor, the fluid pressure sensor detects a fluid pressure of the fluid pump, the fluid flow sensor measures a fluid flow rate of the fluid pump, and the fluid volume sensor measures a fluid volume of the fluid pump;

wherein the communication interface interfaces with a tooth movement monitor to receive tooth movement data obtained from a force sensor attached to or partially embedded in the interior surface of a facial, lingual, or base wall, or a combination thereof of the mouthpiece, such that the force sensor is adapted to contact a side of the at least one tooth, which is opposite a side of the tooth adapted to be in contact with the force exerting member;

wherein the fluid pressure, flow, and volume measurements are used by the controller in conjunction with the tooth movement data to control the operation of the force exerting member.

2. The electronic control console of claim 1, wherein the controller of the electronic control console is programmable.

3. The electronic control console of claim 1, wherein the communication interface allows data communication with a communication device operated by the patient, thereby allowing at least one of a distance the at least one tooth has moved and a current position of the at least one tooth, whether in real time or stored, to be communicated by the communication device of the patient to a remotely located communication device of a remotely located dentist or other user.

4. The electronic control console of claim 3, wherein the communication interface allows receipt of program instructions from the remotely located communication device operated by the dentist or other user, via the communication device operated by the patient, the program instructions programming the controller of the control console.

5. The electronic control console of claim 1, wherein the communication interface allows receipt of program instructions from a remotely located communication device operated by a dentist or other user, the program instructions programming the controller of the control console.

6. The electronic control console of claim 1, wherein the communication interface allows a dentist or other user to remotely access the control console and the at least one orthodontic appliance, via a communication device operated by the dentist and a communication device operated by a patient, to initiate a real time measurement of at least one of a distance the at least one tooth has moved and a current position of the at least one tooth, or obtain the at least one of the distance the at least one tooth has moved and the current position of the at least one tooth stored in the controller of the control console.

* * * * *